(12) United States Patent
Davis et al.

(10) Patent No.: US 11,464,909 B2
(45) Date of Patent: Oct. 11, 2022

(54) SYRINGE TIP CAP

(71) Applicant: Avent, Inc., Alpharetta, GA (US)

(72) Inventors: Benjamin M. Davis, Woodstock, GA (US); David A. Doornbos, Woodstock, GA (US)

(73) Assignee: Avent, Inc., Alpharetta, GA (US)

(*) Notice: Subject to any disclaimer, the term of this patent is extended or adjusted under 35 U.S.C. 154(b) by 302 days.

(21) Appl. No.: 16/675,646

(22) Filed: Nov. 6, 2019

(65) Prior Publication Data
US 2020/0139049 A1    May 7, 2020

Related U.S. Application Data

(60) Provisional application No. 62/757,008, filed on Nov. 7, 2018.

(51) Int. Cl.
*A61M 5/31* (2006.01)
*A61M 39/10* (2006.01)

(52) U.S. Cl.
CPC ....... *A61M 5/31* (2013.01); *A61M 2005/3104* (2013.01); *A61M 2039/1033* (2013.01); *A61M 2039/1088* (2013.01)

(58) Field of Classification Search
CPC ............ A61M 5/31; A61M 2005/3104; A61M 2039/1033; A61M 5/008; A61M 2005/3106; A61M 2005/3215
See application file for complete search history.

(56) References Cited

U.S. PATENT DOCUMENTS

| 10,688,251 B2 * | 6/2020 | Davis ................. A61M 5/3202 |
| 2017/0173321 A1 * | 6/2017 | Davis .................... A61M 39/10 |

* cited by examiner

*Primary Examiner* — Bradley J Osinski
(74) *Attorney, Agent, or Firm* — Dority & Manning, P.A.

(57) ABSTRACT

A tip cap including a central body extending between a first end and a second end. The first end includes a syringe coupling and the second end can include a projection or pivot. In example embodiments, axial engagement of an end connector of a syringe with the syringe coupling self-connects the tip cap with the end connector of the syringe while rotating about the pivot. According to example embodiments, a flange extends outwardly from the central body to define a width or side-to-side dimension. In example embodiments, the minimum side-to-side dimension is about 1.25 inches.

10 Claims, 21 Drawing Sheets

SYRINGE TIP CAP

RELATED APPLICATION

This application claims priority to U.S. Provisional Application No. 62/757,008 entitled "Syringe Tip Cap," filed on Nov. 7, 2018, the contents of which are incorporated herein by reference.

FIELD OF THE INVENTION

The present invention relates generally to the field of medical devices, equipment and supplies, and more particularly to a tip cap for capping a syringe or the like.

BACKGROUND

Healthcare patients are commonly given fluids such as medication and nutrients by being connected to enteral fluid-delivery systems via fluid vessels. Common fluid vessels for delivering such fluids include small-bore tubes and catheters. A problem arises when these fluid tubes are misconnected. That is, when a tube from one fluid delivery system is connected to a tube intended for connection to another fluid delivery system that serves a completely different function, for example, when a feeding administration set is inadvertently connected to a tracheostomy tube. Such tubing misconnections are also referred to as LUER misconnections, small-bore misconnections, or wrong-route errors. Tubing misconnections have resulted in patient injury and deaths, and are widely recognized as underreported.

An underlying cause of these misconnections has been attributed to the universal design of LUER connectors, which are one of the most commonly used types of small-bore connectors in healthcare. These connectors used to connect the tubing of one medical device to another. However, the simple design and ease of use of LUER connectors allows the tube of the device for one delivery system to be connected to tube of an unrelated system that has a different intended use (e.g., vascular, enteral, respiratory, epidural, or intrathecal), resulting in healthcare providers inadvertently connecting wrong systems together and thereby causing liquids (e.g., medications or enteral feedings) or gases (e.g., oxygen) to be delivered through the wrong route.

Efforts are underway to develop standards, such as the ISO 80369 standards, for tubing connections. These standards hold the promise of significantly addressing the tubing misconnection problem. For example, these standards provide for a new connector for enteral feeding tubes that prevents misconnection to non-enteral connectors. This new connector is also referred to as the ENFit connector.

In addition to the ENFit connector being implemented on enteral feeding tubes, the syringes that contain and deliver the fluids (nutrients or medicine) will generally also have the ENFit connector to provide for connection with the tubes. In many cases, a plurality of syringes are filled and capped or sealed in batches. Commonly, the cap or protector that is used to temporarily seal a syringe is small in size and is designed to be coupled to the connector of the syringe in a particular orientation. Some caps have been developed to "self-right" or orientate a particular way (i.e., with their coupling feature face up) when dropped onto a surface, such that connecting the cap with the syringe is relatively easy and quick. In some cases, the caps that "self-right" are relatively small and can pose as a choking hazard to patients, thereby causing some clinicians and others in the medical field to limit their use of the same. Some larger caps have been developed, which are sized so as to not be a choking hazard, but these caps are not compatible with the ENFit connector standards and require further assembly steps and manual manipulation for secure attachment.

Continued improvements to caps or protectors are sought. It is to the provision of a choke-resistant tip cap meeting these and other needs that the present invention is primarily directed.

SUMMARY OF THE INVENTION

In example embodiments, the present invention provides a choke-resistant tip cap including a body extending from a first end to a second end, a syringe connector formed at the first end, and a pivot or projection formed at the second end. In example embodiments, the syringe connector includes an outer collar surrounding a male hub.

In one aspect, the present invention relates to a choke-resistant tip cap including a central body extending between a first end and a second end. The first end includes a syringe coupling defining an outer collar having a threaded inner surface and a male hub centrally-positioned within the outer collar. A flange can be provided, which generally surrounds at least a portion of the central body and is positioned between the first and second ends. According to one example embodiment, flange defines a minimum side-to-side dimension of about 1.25 inches.

The present invention is directed to a tip cap including: a body extending from a first end to a second end; a syringe connector formed at the first end, the syringe connector comprising an outer collar surrounding a male hub, the male hub comprising a recess defined therein and having a floor surface, and an inner surface of the outer collar is threaded; and a pivot formed at the second end of the body, the pivot generally being centrally-positioned and axially aligned with the male hub so as to provide a hands-free assembly when an end connector of a syringe is forced against the syringe connector.

In one particular embodiment, the end connector of the syringe can include at least one thread portion for engagement with the threaded inner surface of the outer collar of the syringe connector. Moreover, with the pivot resting against a support surface and with the syringe connector generally positioned upright and extending in a direction away from the support surface, the end connector of the syringe can be engaged with the syringe connector, thereby engaging the at least one thread portion of the end connector with the threaded inner surface of the outer collar, and wherein further engagement of the end connector with the syringe connector can cause the at least one thread portion to slide along the threaded inner surface of the syringe connector so as to cause rotation of the body about the pivot, thereby assembling the tip cap with the end connector of the syringe with a single end connector-to-syringe connector operation.

In another embodiment, the tip cap can further include a flange extending outwardly from the body, the flange generally positioned between the first and second ends of the body. Moreover, the flange can be configured to provide a seal.

In an additional embodiment, the syringe connector can be compatible with the ENFit and ISO 80369-3 design standards.

The present invention is further directed to a tip cap including: a central body extending between a first end and a second end; a syringe coupling provided at the first end of the body, the syringe coupling including an outer collar having an inner surface defining a threaded surface and a male projection centrally-positioned within the outer collar; a central projection provided at the second end of the body, the central projection generally extending in a direction substantially opposite the first end; and a flange portion generally surrounding at least a portion of the central body and generally being positioned between the first and second ends.

In one particular embodiment, with the second end resting atop a support surface, an end connector of a syringe can be engaged with the syringe coupling of the first end such that an outwardly-extending lug of the end connector engages with the threaded surface, thereby causing the body to rotate atop the support surface about the central projection such that the syringe coupling of the first end can rotatably connect with the end connector of the syringe.

In another embodiment, the flange portion can be substantially cylindrical and outwardly-extends from the central body so as to not pose as a choking hazard.

In an additional embodiment, the flange includes a minimum side-to-side dimension of about 1.25 inches.

In a further embodiment, the syringe connector can be compatible with the ENFit and ISO 80369-3 design standards.

In yet another embodiment, the flange portion can be configured to provide a seal.

The present invention is further directed to a method of connecting a tip cap with an end connector of a syringe, the method including the steps of: providing a tip cap, the tip cap including a body having a syringe connector at one end and a pivot defining a central point of rotation at the other end, the syringe connector including an outer collar surrounding a male hub, the male hub including a recess defined therein and having a floor surface, and an inner surface of the outer collar is threaded; providing a syringe having a generally elongate barrel having an open end for receiving a plunger and a closed end having an end connector, the end connector having a projection formed on an outer surface of the end connector; placing the tip cap atop a support surface such that the pivot is generally in contact therewith; grasping the syringe; and engaging the end connector with the syringe connector of the tip cap.

In one particular embodiment, with the syringe being moved towards the syringe connector, the projection of the end connector can ride along the threaded inner surface, thereby causing to tip cap to rotate about the central point of rotation and further entrance of the projection along the threaded inner surface.

In another embodiment, the pivot can include a post.

In an additional embodiment, the pivot can include a convex surface.

In a further embodiment, axial engagement of the end connector with the syringe connector can cause the tip cap to self-connect itself to the end connector.

In yet another embodiment, after the pivot of the tip cap is generally facing and engaged with the support surface, the tip cap need not be touched for its attachment to the end connector of the syringe.

In one more embodiment, a single one-handed operation of the end connector of the syringe engaging the syringe connector of the tip cap can allow for sealingly attaching the tip cap to the end connector.

These and other aspects, features and advantages of the invention will be understood with reference to the drawing figures and detailed description herein, and will be realized by means of the various elements and combinations particularly pointed out in the appended claims. It is to be understood that both the foregoing general description and the following brief description of the drawings and detailed description of example embodiments are explanatory of example embodiments of the invention, and are not restrictive of the invention, as claimed.

DETAILED DESCRIPTION OF THE INVENTION

Figure 1:
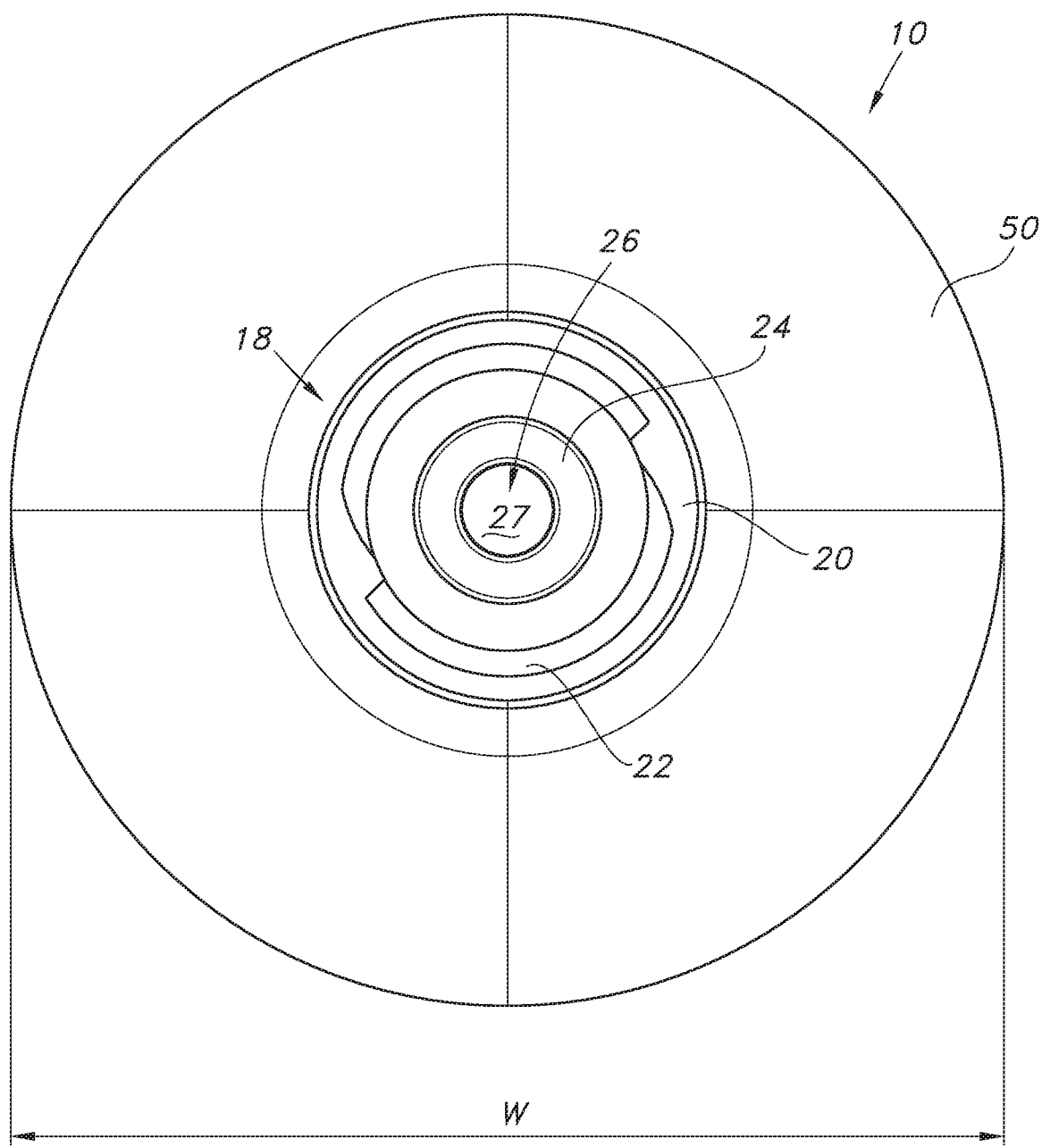
FIG. 1 illustrates a top view of a tip cap according to an example embodiment of the present invention.
Figure 2:
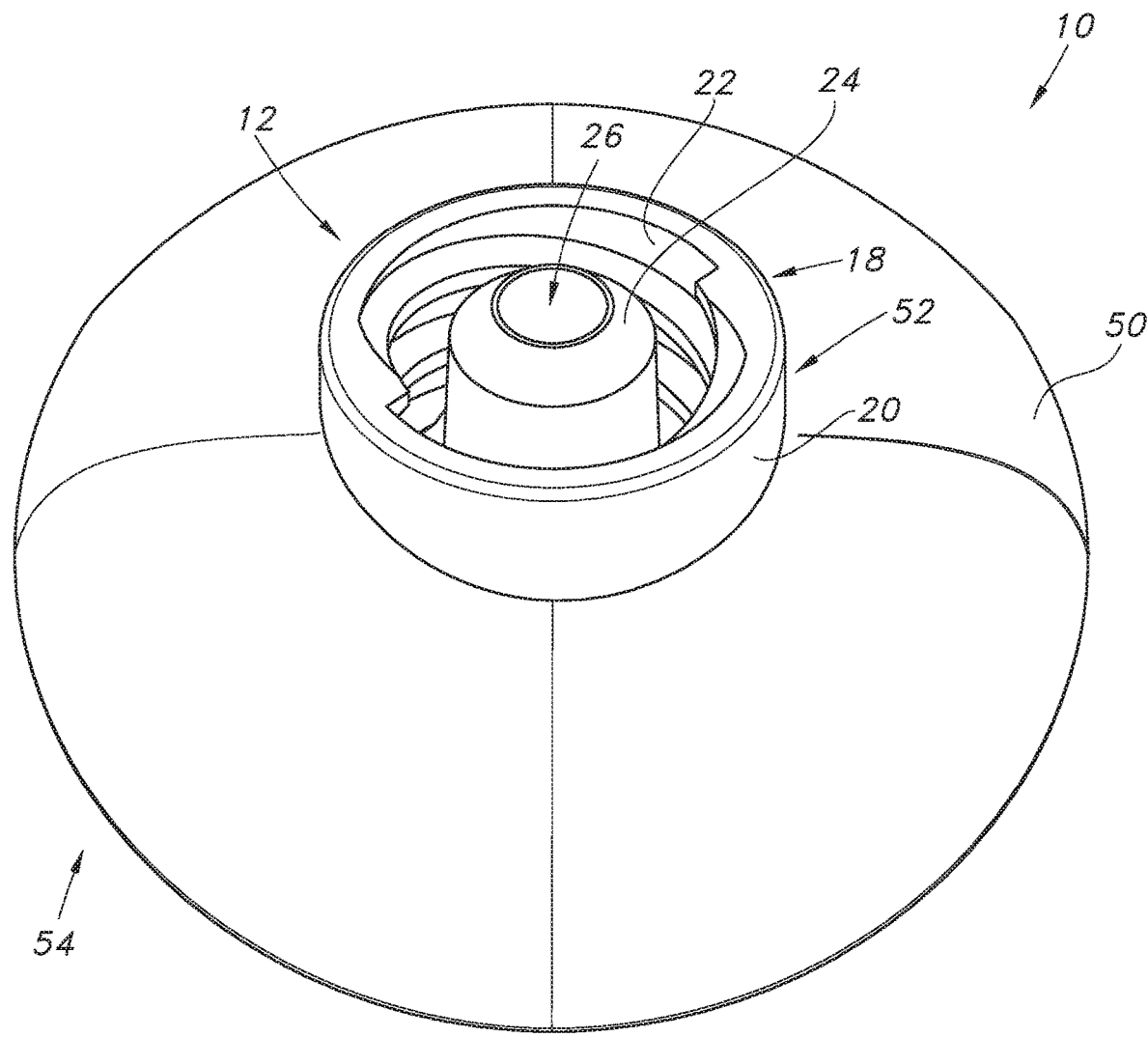
FIG. 2 illustrates a perspective view of the tip cap of FIG. 1.
Figure 3:
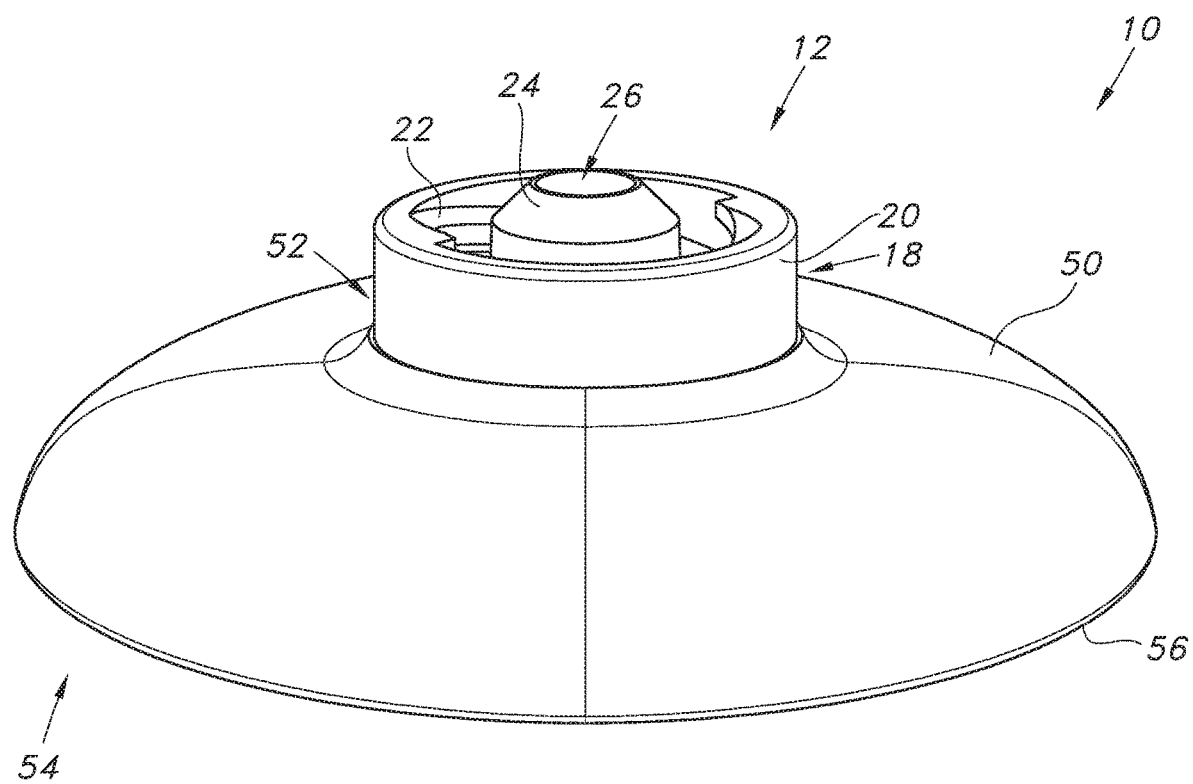
FIG. 3 illustrates a side view of the tip cap of FIG. 1.

The present invention may be understood more readily by reference to the following detailed description of example embodiments taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. As used herein, the terms "about," "approximately," or "generally," when used to modify a value, indicates that the value can be raised or lowered by 5% and remain within the disclosed embodiment.

With reference now to the drawing figures, wherein like reference numbers represent corresponding parts throughout the several views, FIGS. 1-6 show a tip cap 10 according to an example embodiment of the present invention. In example embodiments, the tip cap 10 generally comprises a body 18 extending from a first end 12 to a second end 14, wherein the first end 12 comprises a syringe connector and the second end 14 comprises a central projection or pivot 46. According to example embodiments, a collar or flange 50 is positioned between the first and second ends 12, 14 and generally extends outwardly around the entirety of the body 18.

The syringe connector of the first end 12 generally comprises an outer collar 20 and a male hub 24, wherein the male hub 24 is generally centrally-positioned within the outer collar 20. According to some example embodiments, an internal surface of the outer collar 20 comprises one or more threads 22 formed thereon. In example embodiments, the male hub 24 comprises a well or central recess 26, and a floor surface 27 is defined at a lower portion of the recess 26. Accordingly, the syringe connector is preferably configured for providing a sealed connection with an end connector SC of a syringe S (see FIG. 7). According to some example embodiments, the syringe connector SC comprises a lumen extension tip, and connection of the end connector SC with the syringe connector allows for the lumen extension tip to be received within the central recess 26 of the male hub 24. According to some example embodiments, the syringe connector is formatted according to the ISO 80369-3 design standard. According to another example embodiment, the syringe connector is compatible with the ISO 80369-3 design standard, or for example, the syringe connector is compatible with the ENFit design standard.

Figure 4:
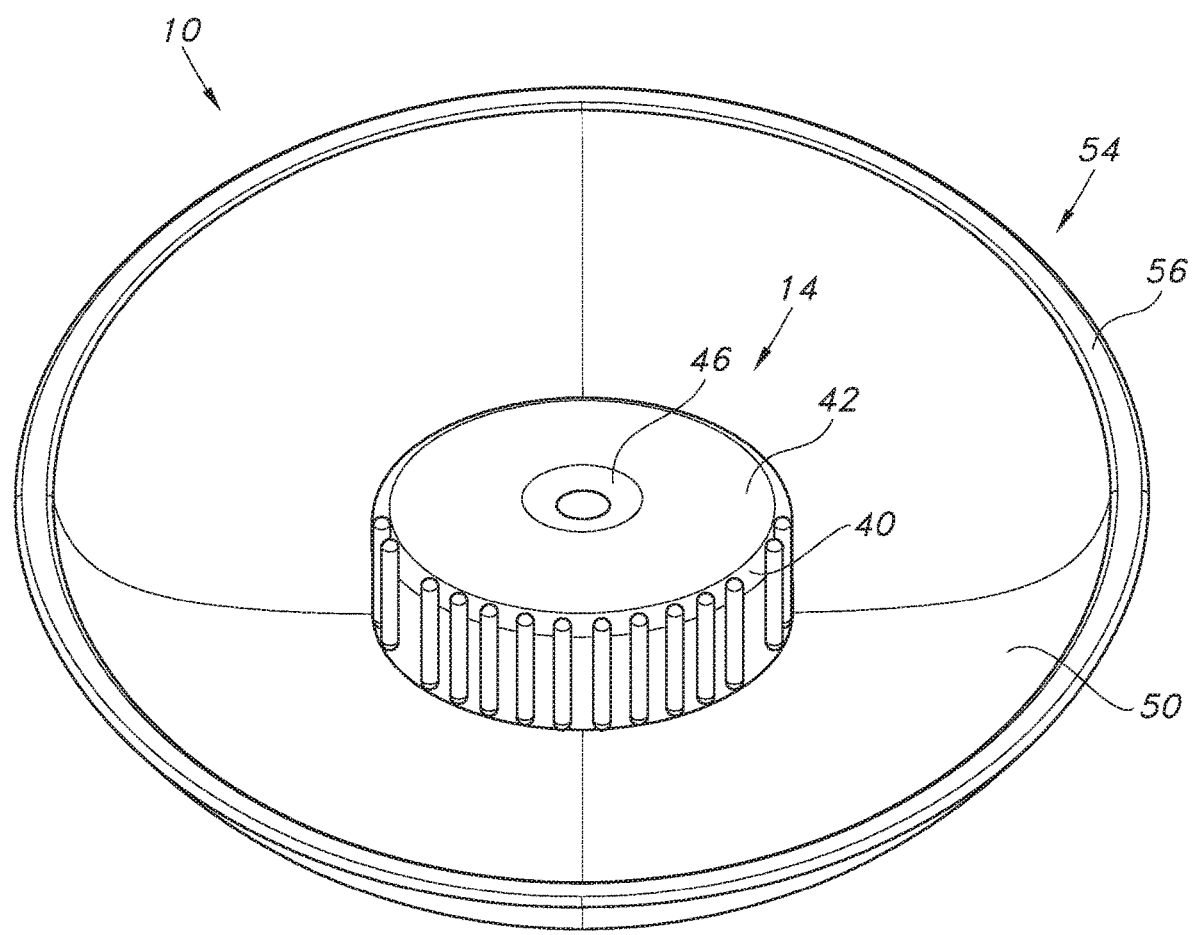
FIG. 4 illustrates a bottom view of the tip cap of FIG. 1.
Figure 5:
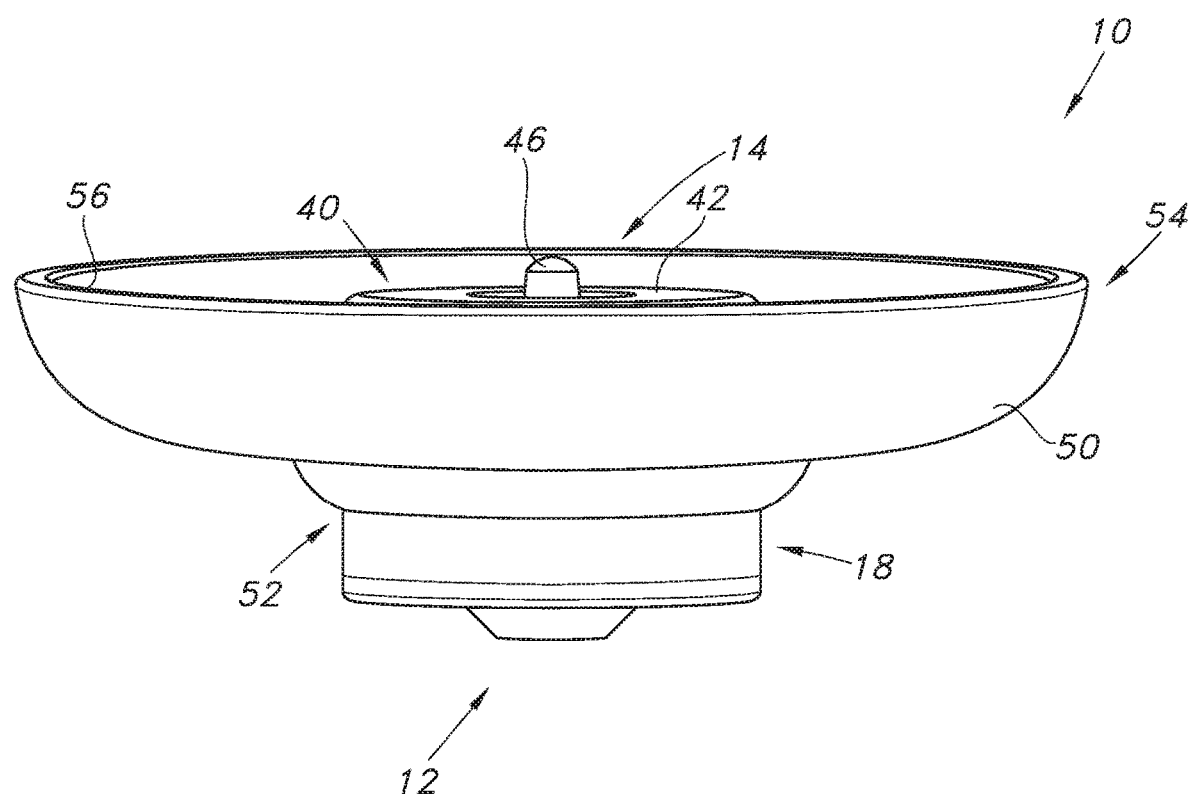
FIG. 5 illustrates a side view of the tip cap of FIG. 1 in an inverted position.
Figure 6:
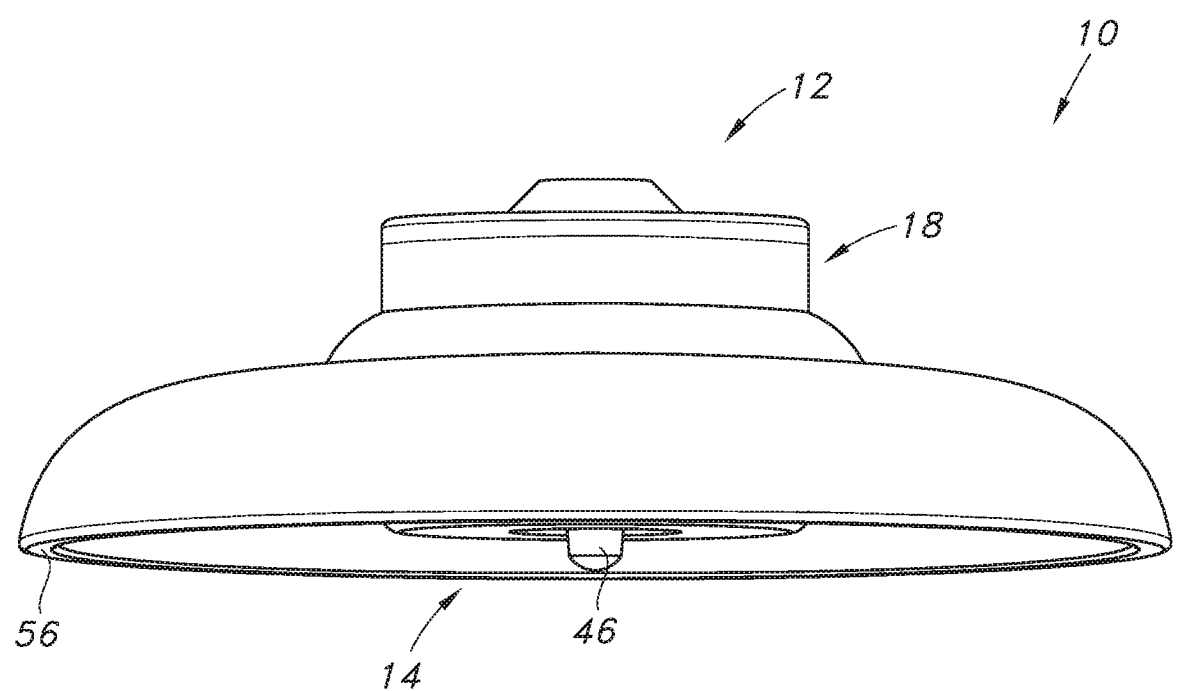
FIG. 6 illustrates another side view of the tip cap of FIG. 1.

As best depicted in FIGS. 4-6, the second end 14 of the body 18 comprises the central projection 46, which as will be described below, preferably allows for a rotational assisted assembly of the tip cap 10 with the end connector SC of the syringe S during assembly. In example embodiments, the second end of the body 18 comprises a cylindrical body 40 comprising an end surface 42, and the central projection 46 extends from the end surface 42 in a direction generally opposite the first end 12. In other example embodiments, the cylindrical body 40 need not be cylindrical, for example, as long as a projection is extending therefrom so as to permit rotation of the cap 10 atop a support surface during assembly (as will be described below).

According to some example embodiments, one or more vents, openings or passageways can be formed with the tip cap 10. According to one example embodiment, one or more openings can be formed with the end surface 42 of the cylindrical body, and can communicate with a recess or annular space that is defined between the outer cylindrical collar 20 and the male hub 24. Thus, according to example embodiments, one or more openings are provided to communicate through the entirety of the body 18, or for example, at least between the end surface 42 of the cylindrical body 40 and the annular recess defined between the outer cylindrical collar 20 and the male hub 24 of the syringe connector. As such, any residual fluids are not trapped within the annular recess and can escape, drain or vent from the tip cap, and thus not promote the growth of bacteria or other unwanted contaminants.

The flange 50 is generally positioned between the first and second ends 12, 14 of the body 18, and extends outwardly therefrom to define a side-to-side width W of about 1.25 inches. According to some example embodiments, to ensure the tip cap 10 is nota choking hazard and to comply with 16 CFR § 1501.4, the minimum side-to-side dimension W is about 1.25 inches. According to alternate example embodiments, the width W can be chosen as desired, for example, less than or equal to 1.25 inches, or for example, greater than 1.25 inches. In example embodiments, the flange 50 comprises a first end 52 that is fitted against the body 18 and a second end 54 that is defined at its outermost portion. For example, according to example embodiments, the first end 52 of the flange 50 is generally positioned near the midpoint of the body 18 and extends outwardly and towards the second end 14 to its second end 54. In example embodiments, the second end 54 of the flange 50 comprises an end surface 56. According to example embodiments and as depicted in FIG. 5, the end surface 56 of the flange 50 is generally positioned below at least a portion of the projection 46. Preferably, the end surface 56 is positioned relative to the second end 14 (and projection 46 thereof) such that at least some space is provided between the end surface 56 and the surface of a support surface when the projection 46 is contacting the surface of the support surface. In example embodiments, the flange 50 can comprises a substantially radiused surface profile, which can comprise one or more convex/concave surface profiles between the ends 52, 54. In other example embodiments, the surface profile of the flange 50 can be chosen as desired.

Figure 7:
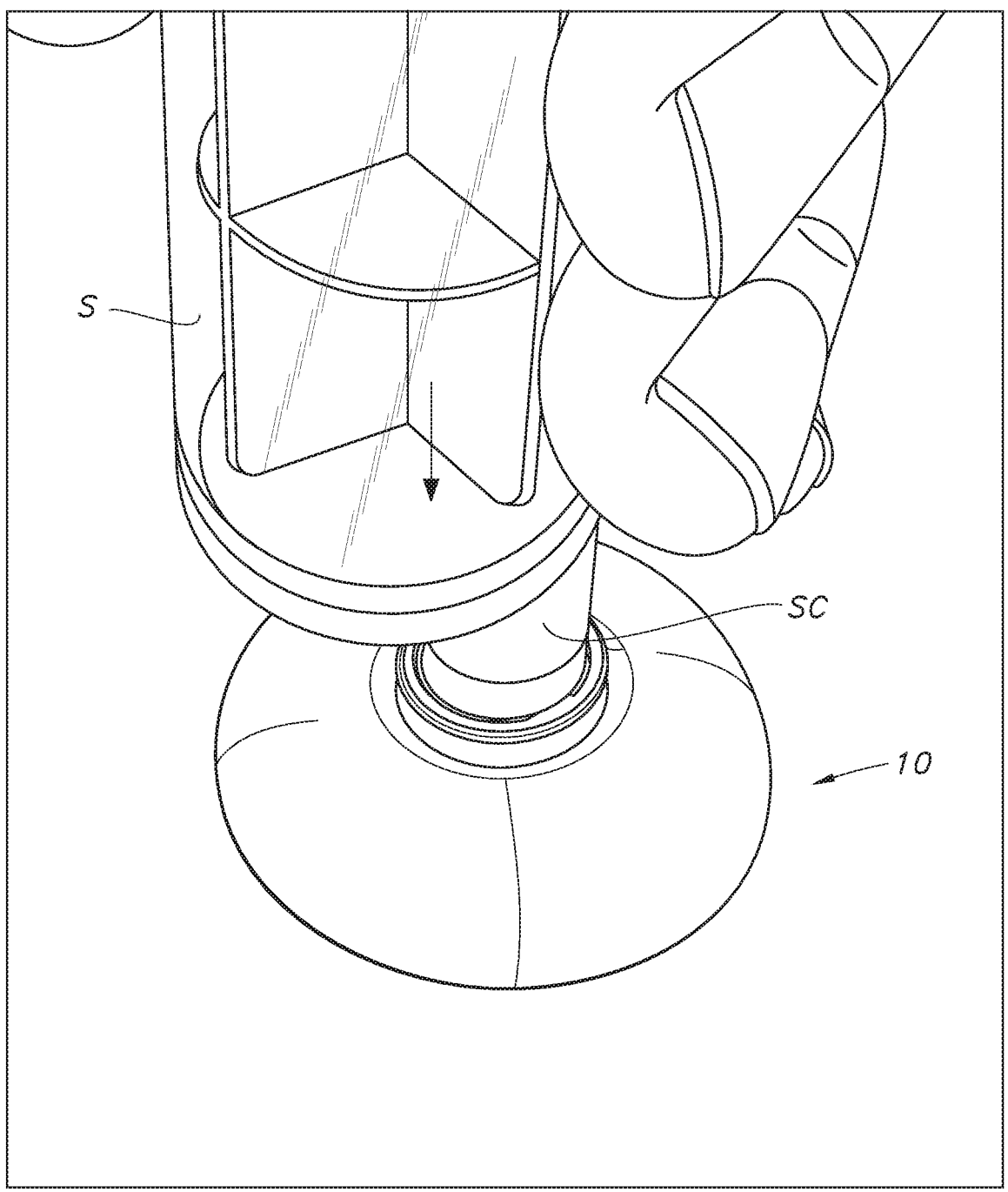
FIG. 7 illustrates attaching the tip cap of FIG. 1 to a syringe by pressing the syringe downward onto the tip cap.
Figure 8:
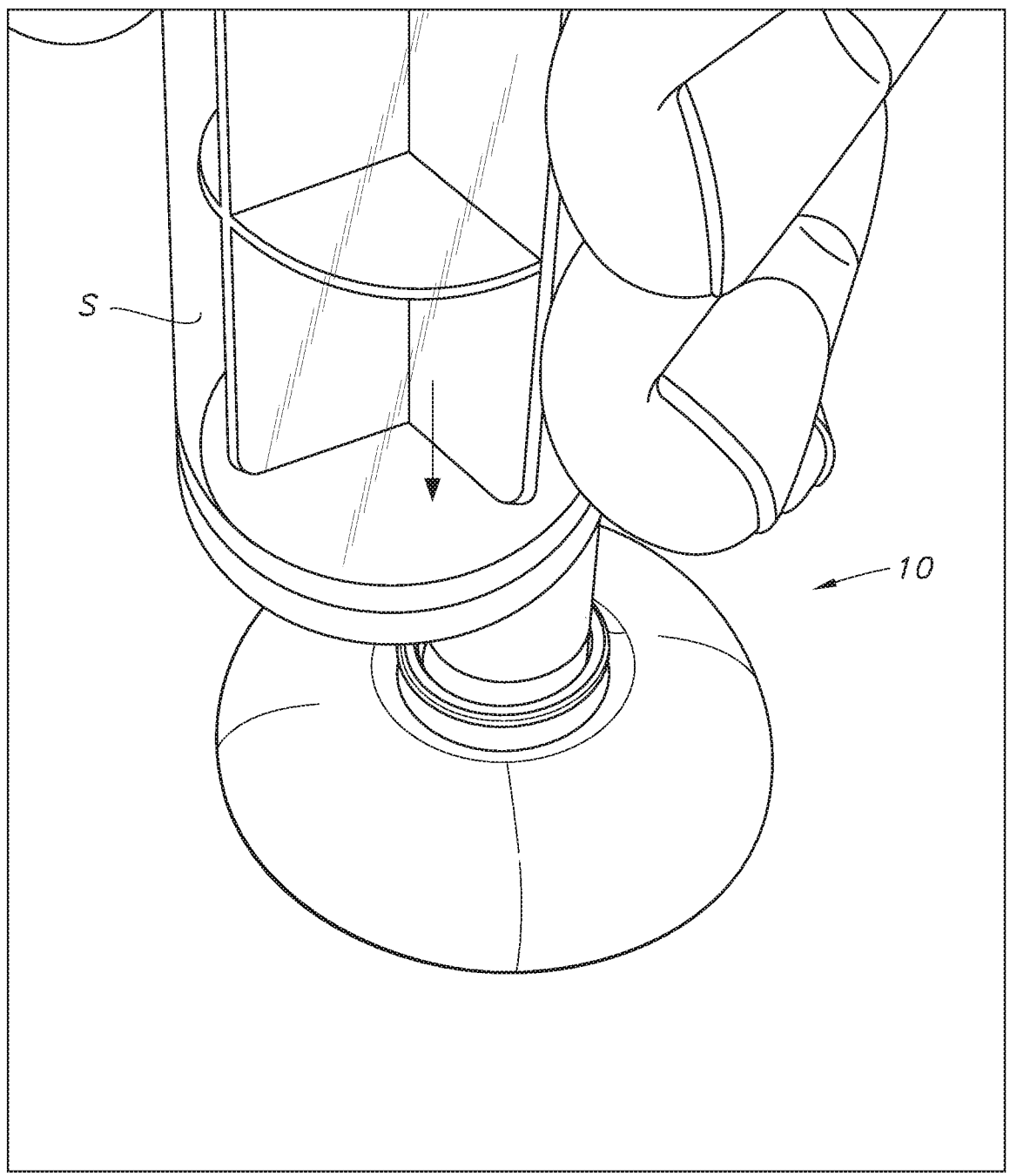
FIG. 8 illustrates a zoomed-in view of FIG. 7.
Figure 9:
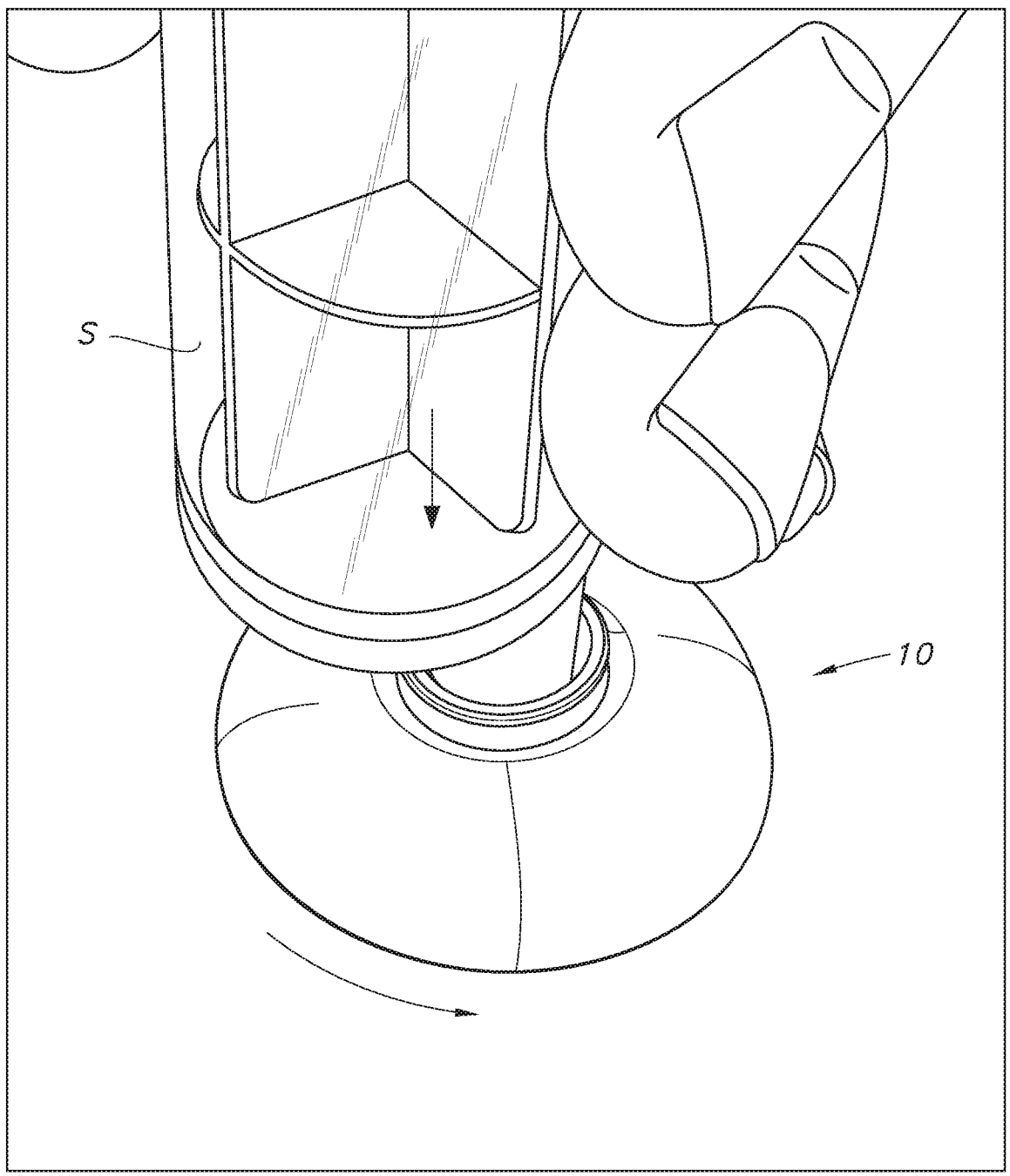
FIG. 9 illustrates the sequence of attaching the tip cap of FIG. 1 to a syringe including rotation of the tip cap.
Figure 10:
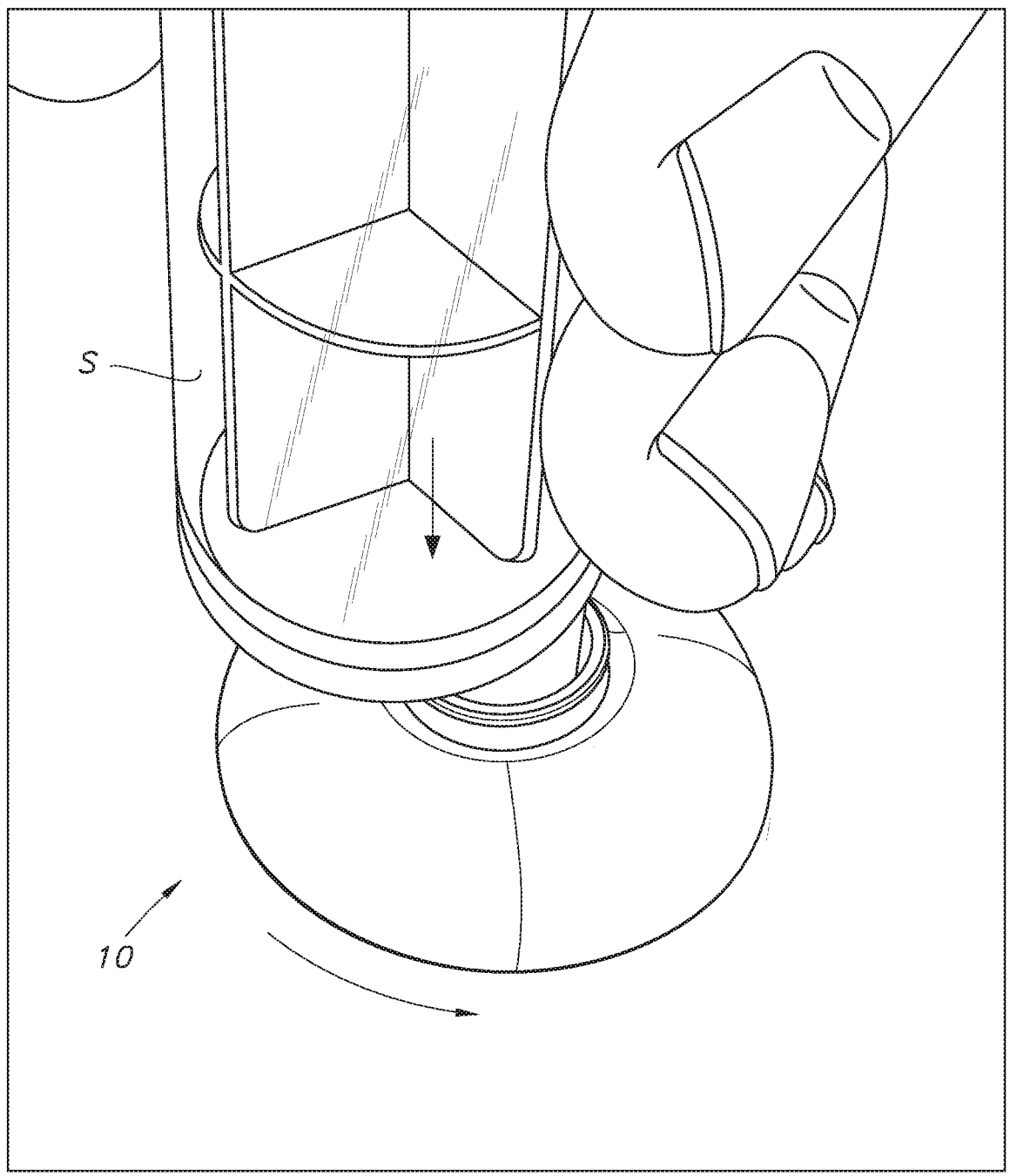
FIG. 10 illustrates a zoomed-in view of FIG. 9.
Figure 11:
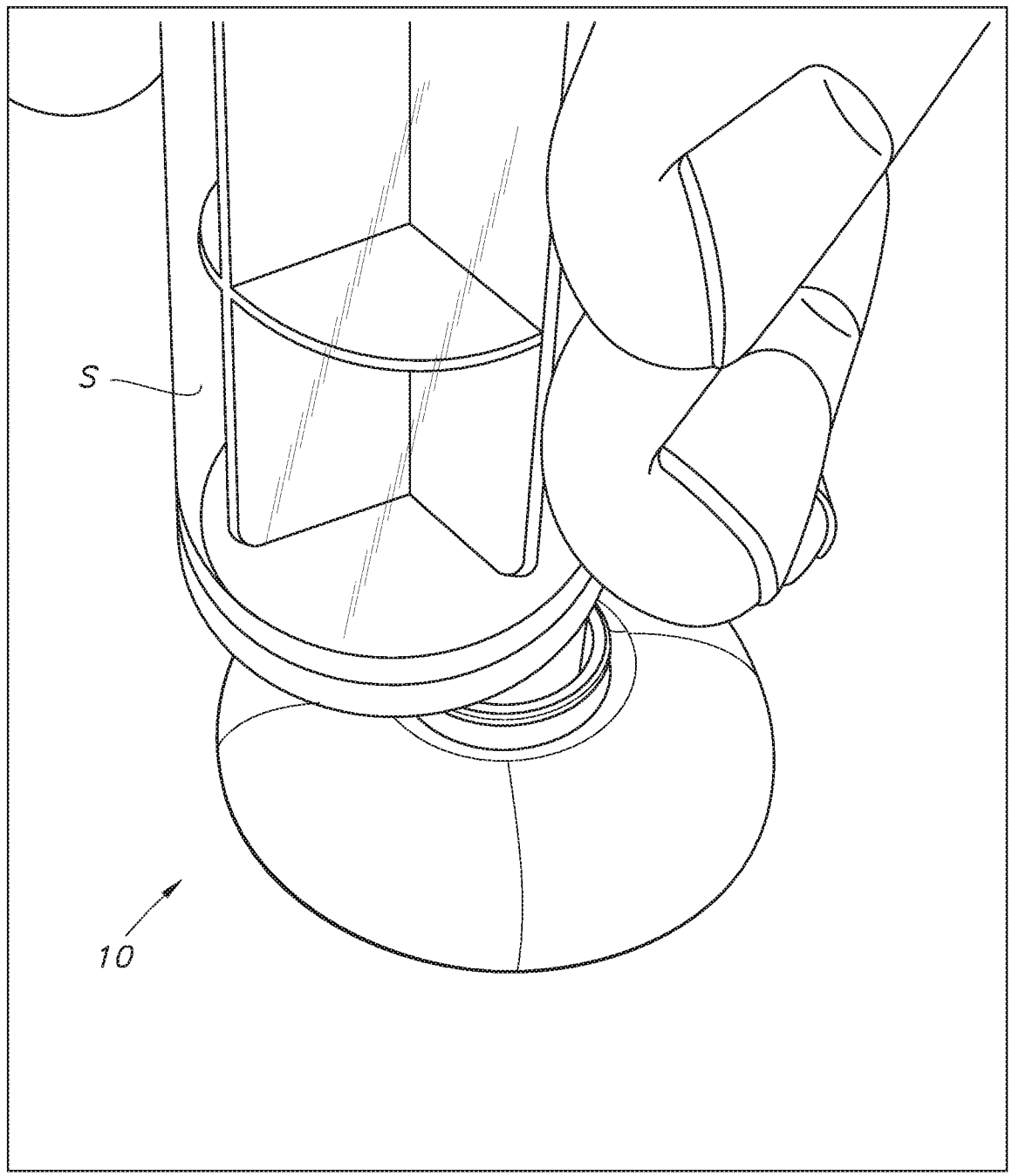
FIG. 11 illustrates the tip cap and syringe of FIG. 7 in an attached configuration.

FIGS. 7-11 show a sequence of operation of the tip cap 10 with the end connector SC of the syringe. According to example embodiments, the end connector SC of the syringe S comprises a female coupling. According to some example embodiments, the female coupling is ISO 80369-3 compatible, or for example, compatible with the ENFit design standard. IN some example embodiments, the female coupling of the end connector SC comprises one or more lugs formed on an outer surface thereof, which are preferably compatible and engageable with the threads 22 of the inner surface of the outer collar 20. As depicted in FIG. 7, with the tip cap 10 resting atop a support surface, the end connector SC engages with the syringe connector of the tip cap 10. In example embodiments, the syringe S is pressed in a direction towards the support surface and against the syringe connector, thereby allowing the tip cap 10 to rely on being supported by the projection 46. Thus, further movement of the syringe S (and end connector SC) against the syringe coupling allows the tip cap 10 to pivot about the projection 46, and thus, allow for rotation of the entirety of the tip cap 10 such that the end connector SC and the syringe coupling further engage and become attached to each other. According to some example embodiments, since the projection 46 comprises a substantially small area, and given that the projection 46 extends the furthest from the second end 14, a very small amount of frictional engagement is provided between the projection 46 and the support surface, and thus, the tip cap 10 is not restricted from rotating. According to some example embodiments, during the engagement of the end connector SC of the syringe S with the syringe coupling, the user controlling the syringe S can somewhat orient the syringe S in a substantially vertical manner such that the entirety of the end surface 56 remains spaced apart from the support surface.

Thus, according to example embodiments, the lugs of the female connector of the end connector SC of the syringe S engage and ride along the threads 22 of the outer collar 20, thereby causing the tip cap 10 to rotate about the projection 46 and relative to the end connector SC until the end connector SC and the syringe coupling are substantially engaged with each other.

Figure 12:
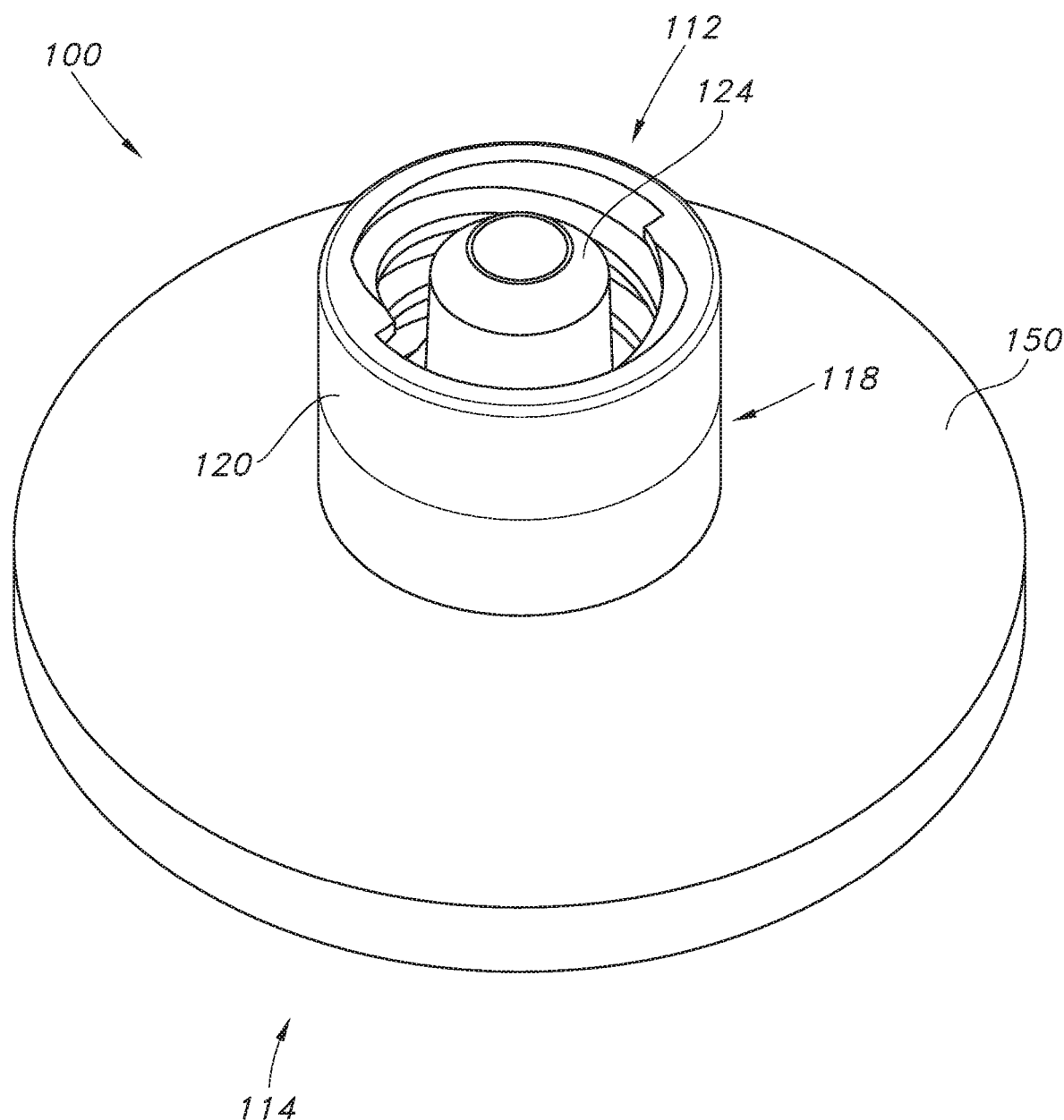
FIG. 12 shows a perspective view of a tip cap according to another example embodiment of the present invention.

FIG. 12 shows a tip cap 100 according to another example embodiment of the present invention. In example embodiments, the tip cap 100 is substantially similar to the tip cap 10. According to one example embodiment, the tip cap 100 comprises a substantially disc-like flange 150, for example, which is generally positioned near the second end 114 of the body 118. Similarly, the first end 112 of the body 118 comprises a syringe coupling having an outer collar 120 and a male hub 124 centrally-positioned within the outer collar 120.

Figure 13:
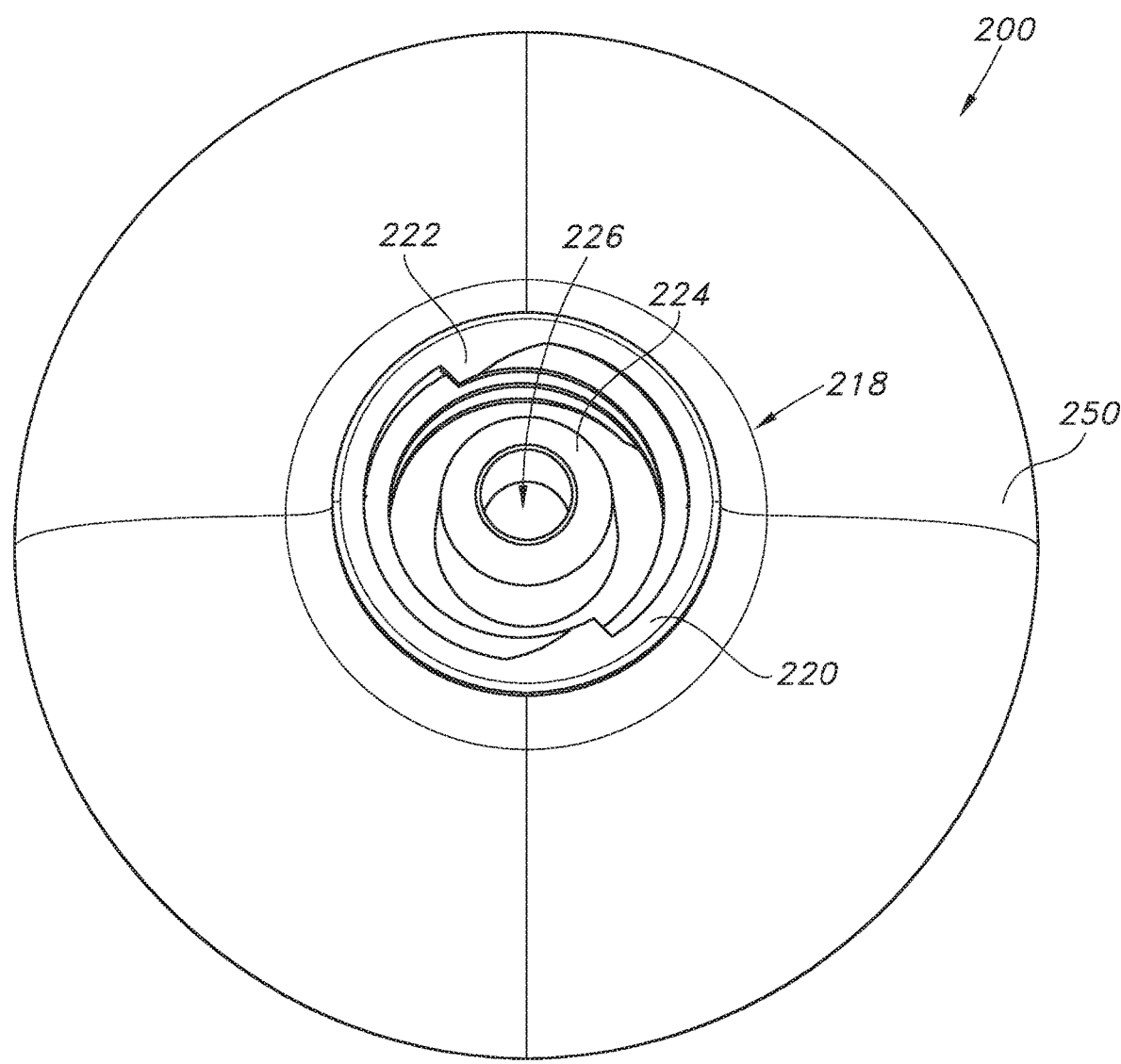
FIG. 13 illustrates a top view of a tip cap according to another example embodiment of the present invention.
Figure 14:
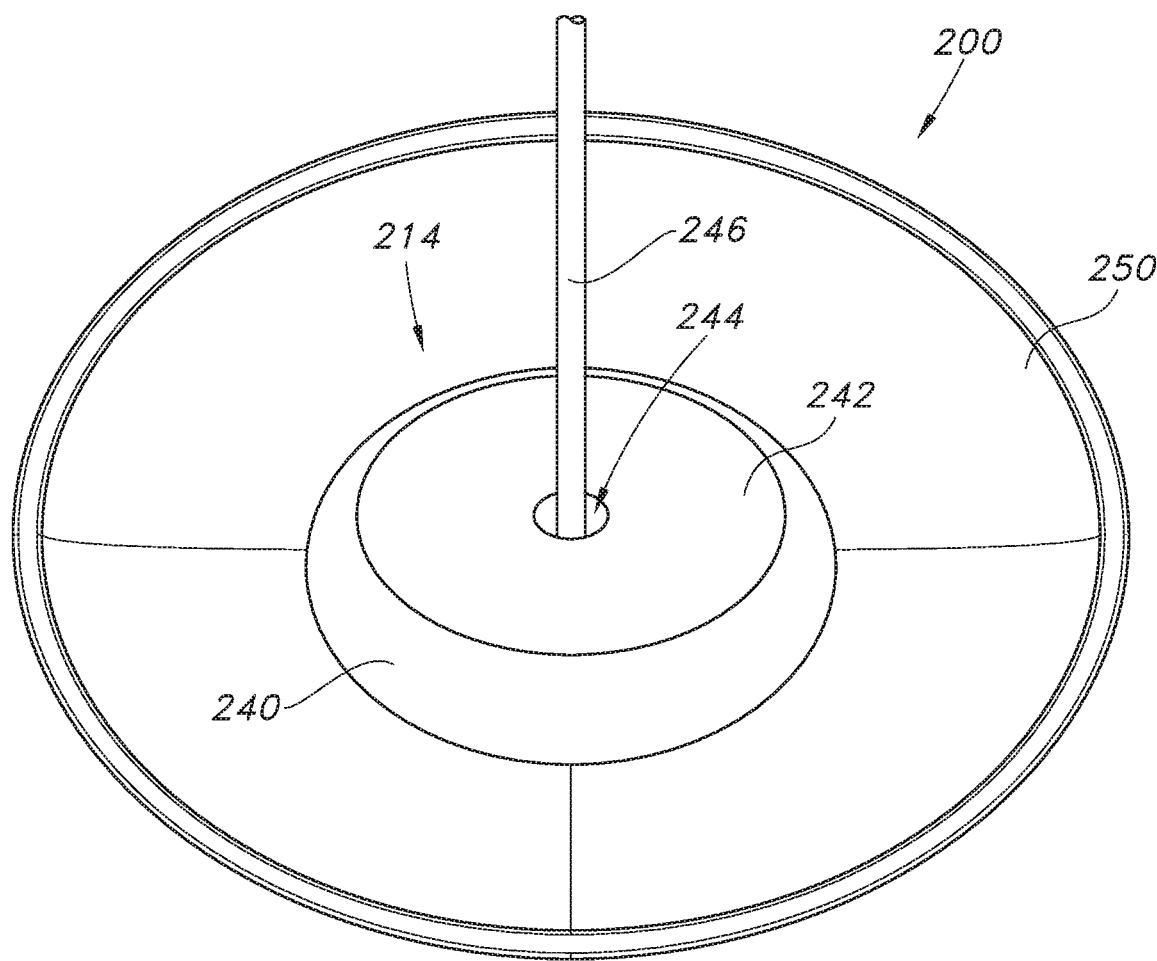
FIG. 14 illustrates a bottom view of the tip cap of FIG. 13.
Figure 15:
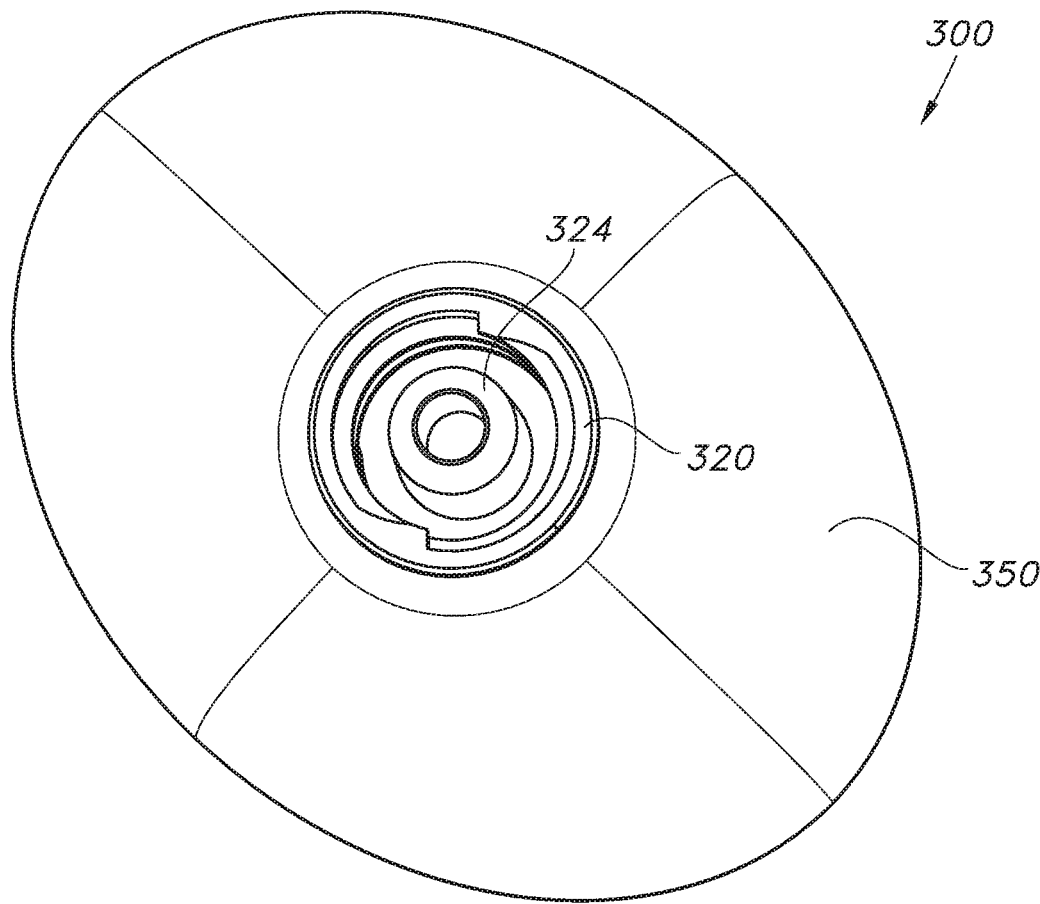
FIG. 15 illustrates a top view of a tip cap according to yet another example embodiment of the present invention.
Figure 16:
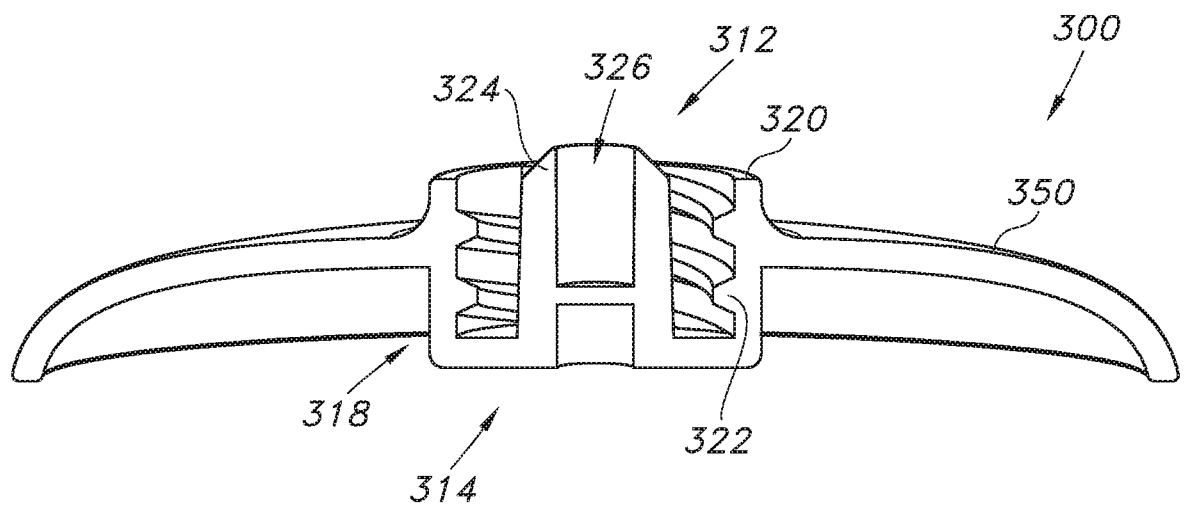
FIG. 16 illustrates a cross-sectional view of the tip cap of FIG. 15.
Figure 17:
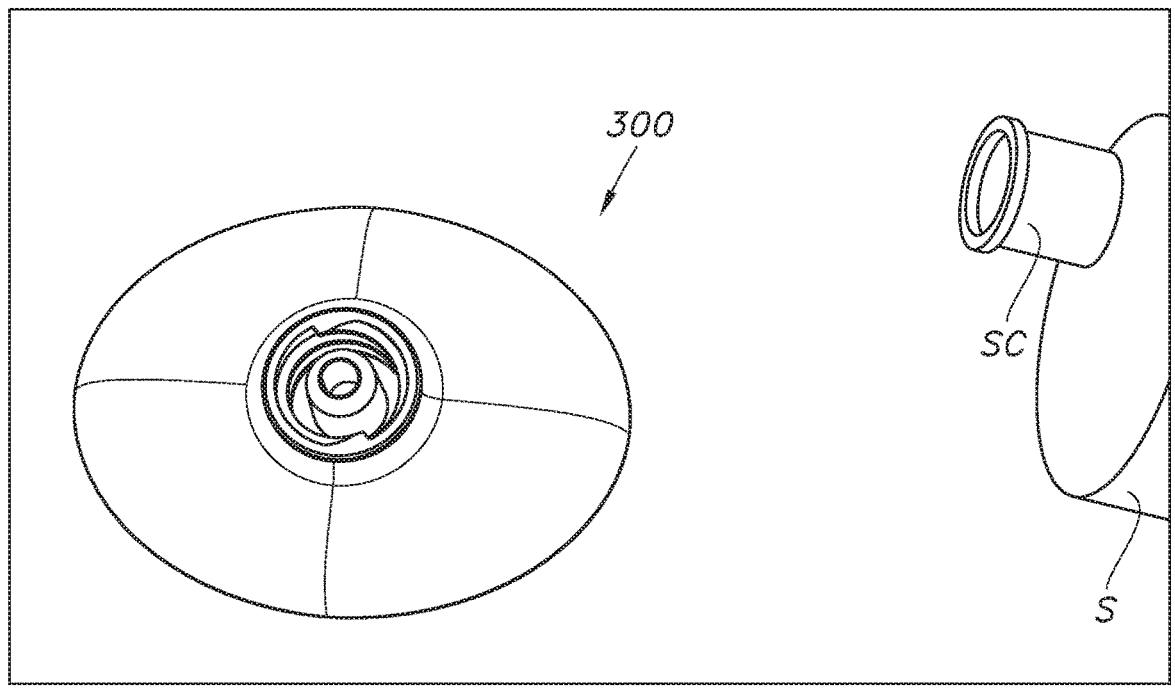
FIG. 17 illustrates the tip cap of FIG. 15 and a syringe prior to attachment of the syringe to the tip cap.
Figure 18:
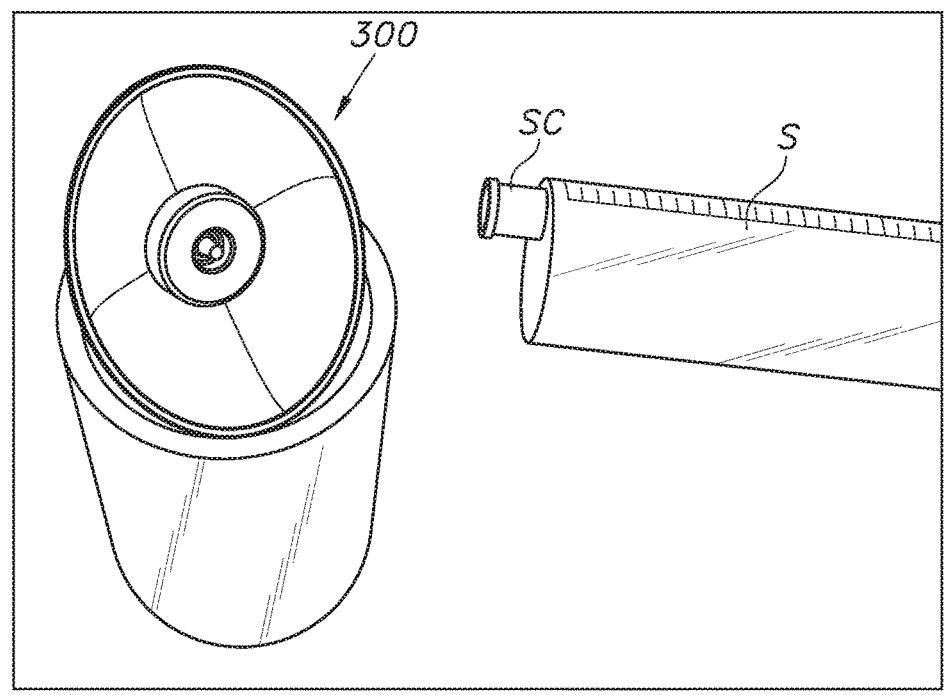
FIG. 18 illustrates the tip cap of FIG. 15 positioned on an opening of a bottle.
Figure 19:
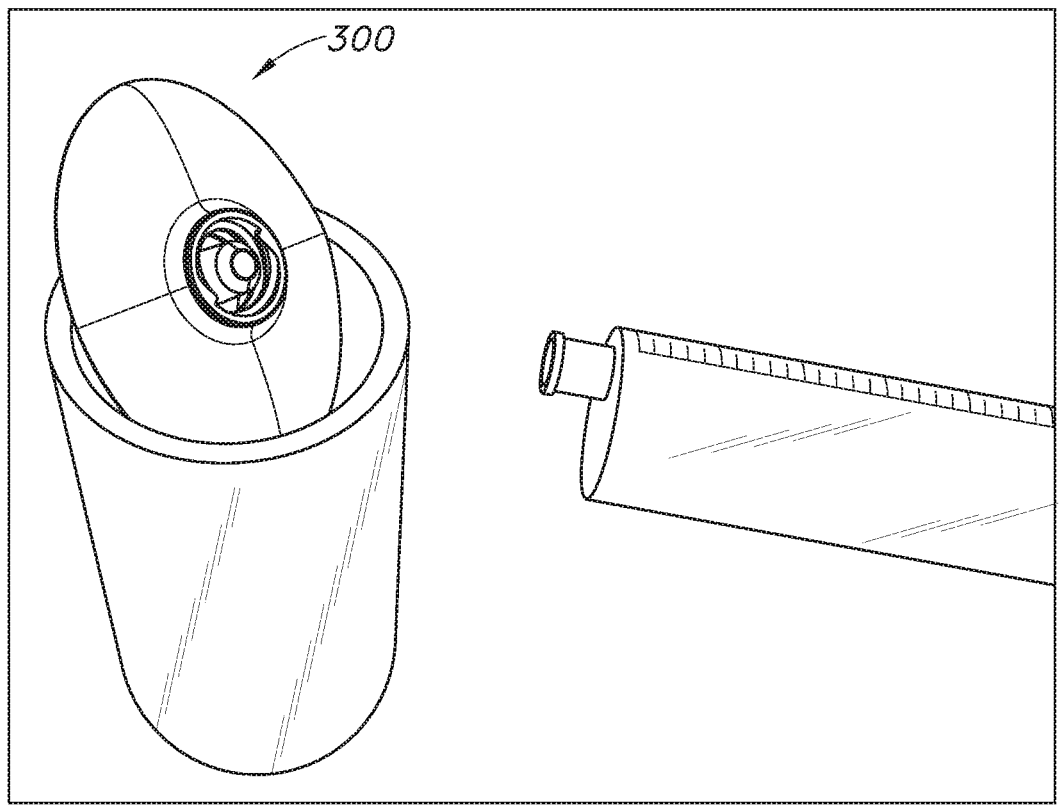
FIG. 19 illustrates the tip cap of FIG. 15 inserted within an opening of a bottle.
Figure 20:
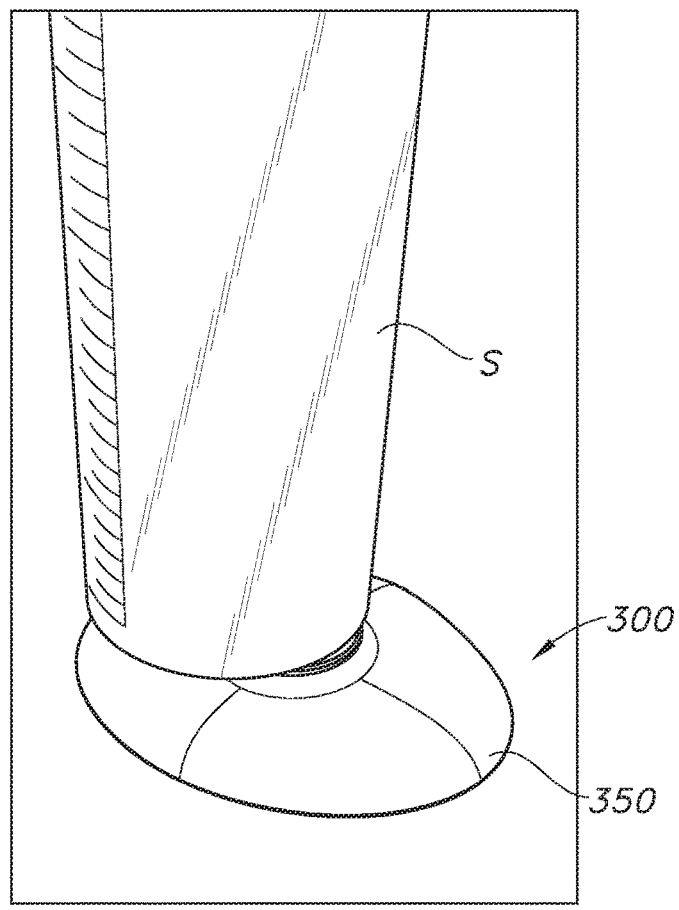
FIG. 20 illustrates the tip cap of FIG. 15 attached to a syringe.
Figure 21:
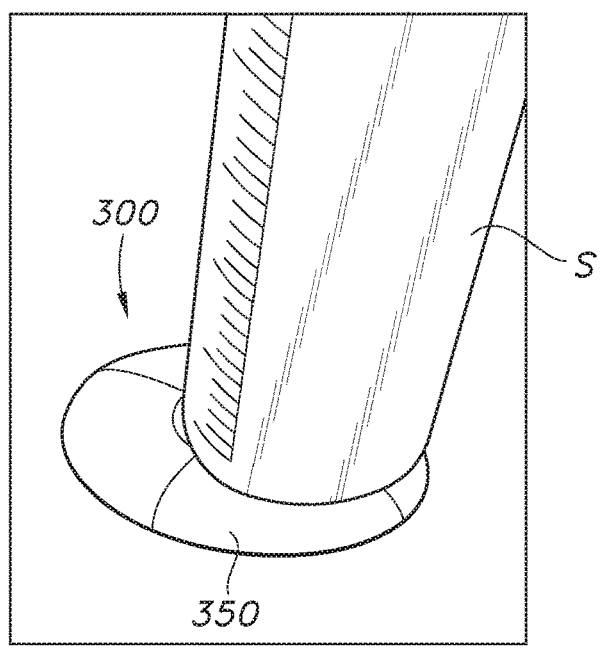
FIG. 21 illustrates an opposite side view of the tip cap and syringe assembly of FIG. 20.

FIGS. 13-14 show a tip cap 200 another example embodiment of the present invention. According to example embodiments, the tip cap 200 is substantially similar to the tip cap 10 as described above. According to one example embodiment, the flange 250 is generally integrally formed with the body 218. According to other example embodiments, the flange 250 can be a separate piece and connected with the body 218. According to another example embodiment, a shallow well or recess 244 is formed within a portion of the end surface or wall 242 of the body 240, for example, which generally surrounds the projection 246.

FIGS. 15-21 show another example embodiment of the present invention. In example embodiments, the tip cap 300 preferably acts as a stand, for example, to support a syringe S connected thereto in a substantially vertical orientation. In example embodiments, the tip cap 300 can preferably have similar features and functionality as described below. According to one example embodiment, the tip cap comprises a body 318 extending from a first end to a second end, and a flange is generally coupled with the body 318 and outwardly extends therefrom. In example embodiments, the flange 350 can define a minimum side-to-side dimension of at least about 1.25 inches. In other example embodiments, the side-to-side dimension can be chosen as desired.

Similarly, the first end can comprise a syringe coupling comprising an outer collar having a threaded inner surface and a male hub centrally-positioned within the outer collar. According to some example embodiments, the threads formed on the inner surface of the outer collar can be configured such that the leading thread is oriented relative to the maximum side-to-side dimension of the flange. For example, according to some example embodiments, the syringe S is intended to larger volumes, and the end connector SC thereof is offset from a central axis of the syringe S. Thus, once the end connector SC is fully connected with the syringe coupling, the orientation of the syringe S is preferably configured to be aligned with the maximum side-to-side dimension (see FIGS. 20-21), and thus, provide sufficient stability so that the syringe S remains in a substantially upright position, thereby preventing the syringe S from tipping over.

Figure 22:
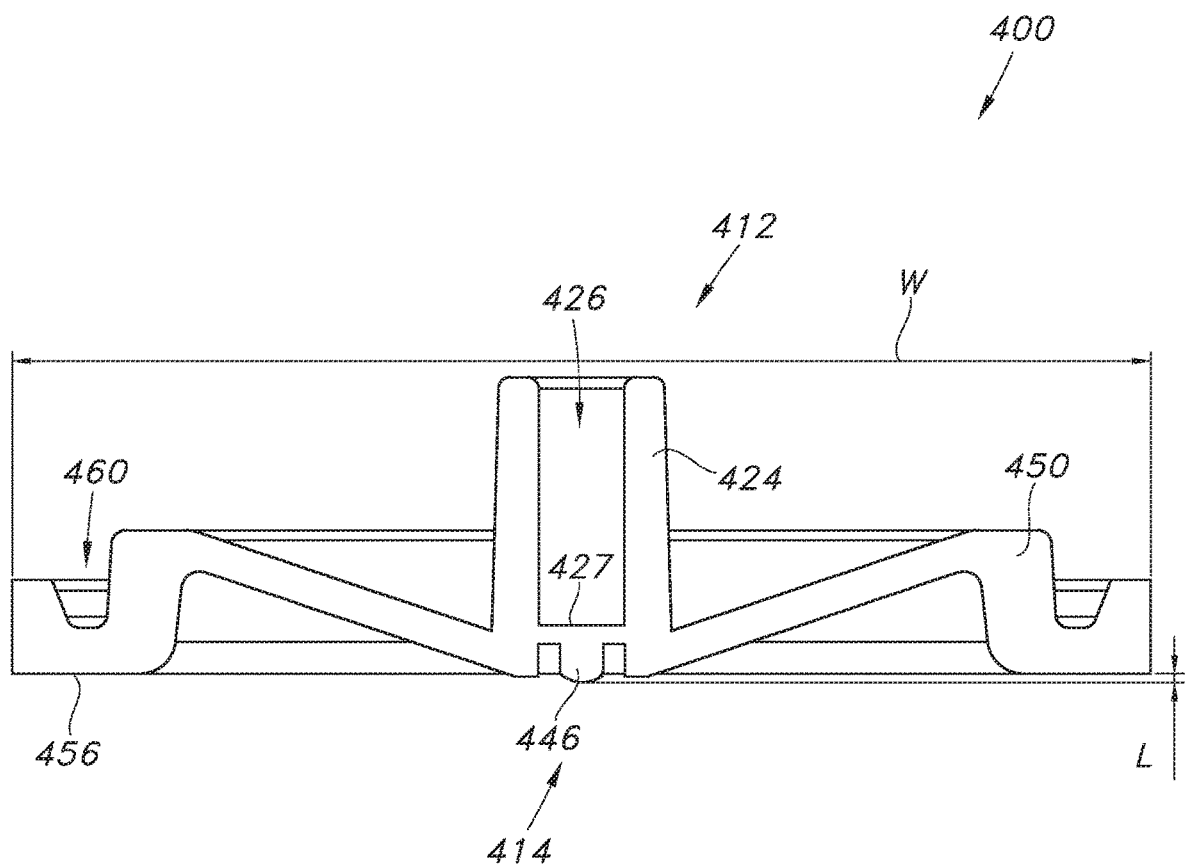
FIG. 22 illustrates a cross-sectional view of a tip cap according to yet another embodiment of the present invention.
Figure 23:
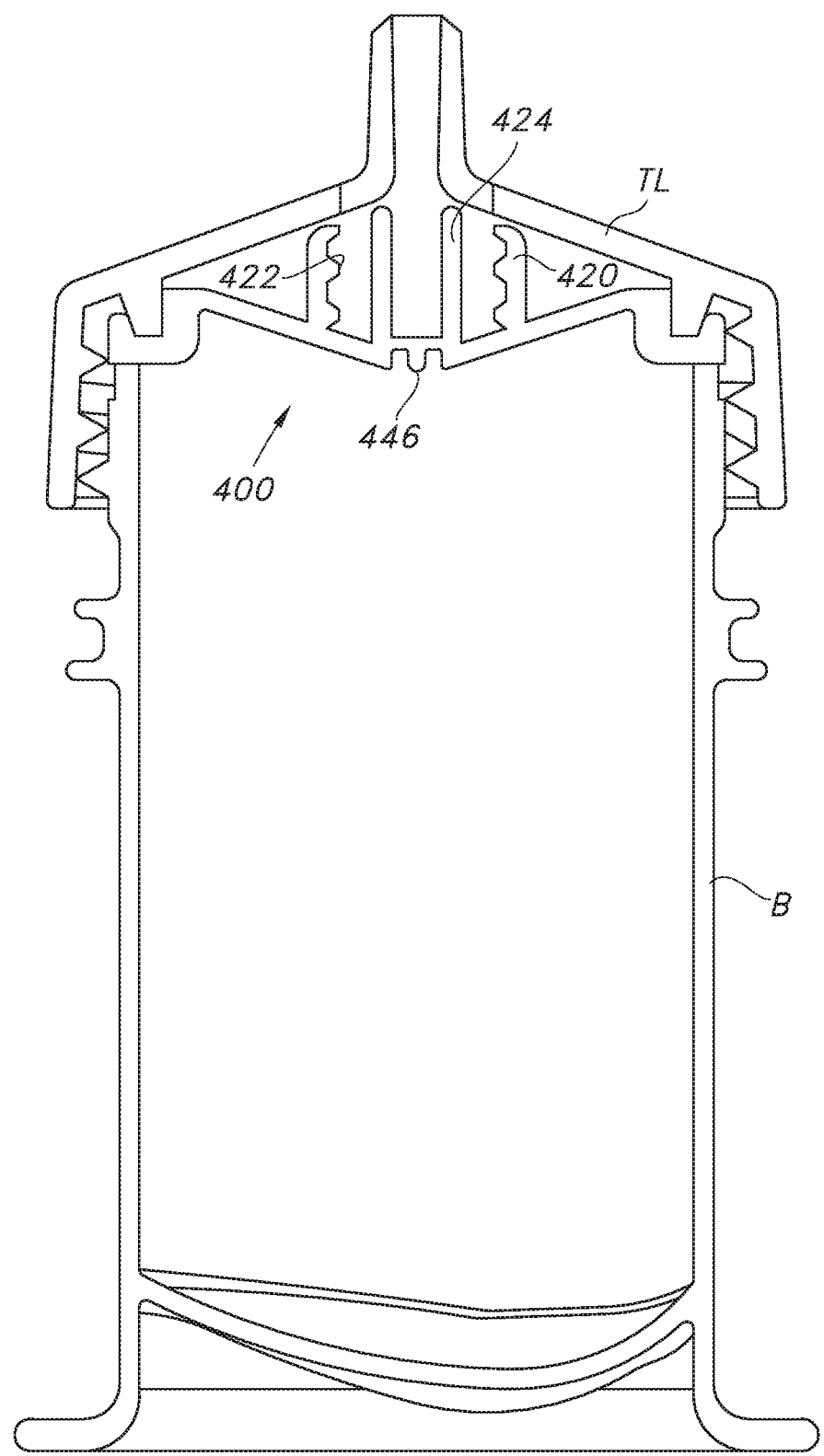
FIG. 23 illustrates a cross-sectional view of the tip cap of FIG. 22 attached to a bottle.

FIGS. 22-23 show a tip cap 400 according to another example embodiment of the present invention. According to example embodiments, the tip cap 400 is generally similar to the tip caps as described above. For example, the tip cap 400 comprises a body extending from a first end 412 to a second end 414, wherein the first end 412 comprises a syringe connector and the second end 414 comprises a central projection or pivot 446. According to example embodiments, a collar or flange 450 generally extends outwardly around the entirety of the body. In example embodiments and as similarly described above, the tip cap 400 preferably comprises a side-to-side dimension W of at least about 1.25 inches. The central projection or pivot 446 is generally configured such that the outermost end portion thereof projects beyond a bottom surface 456 of the flange 450. Thus, as similarly described above, the pivot 446 can act as a point of rotation such that pressing the end connector SC of the syringe S against the syringe connector causes rotation of the tip cap 400 relative to the syringe S, thereby substantially (if not entirely) securing the end connector SC with the syringe connector. According to example embodiments, the pivot 446 extends in a direction generally opposite the first end 412 such that a spacing or length L of between about 0.005-0.01 inches is defined therebetween. In other example embodiments, the length L can be chosen as desired.

As will be described below, the tip cap 400 can preferably be multi-functional, for example, to provide for both acting as a tip cap to attach and seal with an end connector SC of a syringe S and for acting as a seal between a syringe or bottle B and a fluid transfer lid or cap TL (see FIG. 23).

In example embodiments, the syringe connector can be configured as desired, for example, configured to be formatted for compatibility with the ENFit or ISO 80369-3 design standard. As depicted in FIG. 23, the syringe connector comprises outer collar 420 and a male hub 424, wherein the male hub 424 is generally centrally-positioned within the outer collar 420. According to some example embodiments, an internal surface of the outer collar 420 comprises one or more threads 422 formed thereon, for example, which are configured for compatible engagement with one or more lugs or threads formed on an outer surface of the end connector SC of the syringe S. Referring back to FIG. 22, the male hub 424 comprises a well or central recess 426, and a floor surface 427 is defined at a lower portion of the recess 426. Accordingly, the syringe connector is preferably configured for providing a sealed connection with the end connector SC of the syringe S. According to some example embodiments, the syringe connector SC comprises a lumen extension tip, and connection of the end connector SC with the syringe connector allows for the lumen extension tip to be received within the central recess 426 of the male hub 424.

According to some example embodiments, one or more vent channels or grooves can be formed with the male hub 424, for example, so as to provide venting during the attachment of the end connector SC with the syringe coupling. U.S. Provisional Patent Application Ser. No. 62/620,576 discloses a vented enteral connector having one or more grooves or channels formed with a male hub, which is incorporated by reference herein in its entirety. Preferably, the vent channels prevent air from being trapped and compressed between the end connector SC and the syringe connector, thereby preventing plunger pushback, exposure of the elements within the syringe barrel, and any dosing inconsistencies and inaccuracies due to the plunger pushing back.

Referring to FIG. 23, the tip cap 400 is preferably multi-functional to either act as an end cap or tip cap for sealing the end connector SC of the syringe S or for acting as a seal between the bottle B and the fluid transfer lid TL (to be attached to the bottle). In example embodiments, the flange 450 comprises an outer circumferential groove 460 formed therein for receiving a seal or flange of the fluid transfer lid TL. Preferably, with the bottom surface 456 of the flange 450 engaged with an end of the bottle B and the flange of the fluid transfer lid TL received within the groove 460 of the flange 450, a threaded outer collar of the fluid transfer lid TL is attached with the threaded end of the bottle B such that a sealed connection is provided. When it is desired to draw fluids from the bottle B to the syringe S, the tip cap 400 can be removed from between the bottle B and transfer lid TL, and the end connector SC of the syringe S can couple with a central male port of the transfer lid TL. After fluids are drawn into the syringe, the tip cap 400 can then be used for attachment with the end connector SC of the syringe S (e.g., that now has fluids contained therein from the bottle B). A closure or end cap (not shown) can also be provided with the transfer lid TL such that the male port thereof can be sealed after transferring fluids to the syringe S.

According to some example embodiments, the syringe connector need not have the outer cylindrical collar, and thus, the end connector SC of the syringe S is attached with the male hub 424 via a friction or slip fit (see FIG. 22). In some example embodiments, where the outer cylindrical collar 420 is not surrounding the male hub 424, the central projection 446 can be removed, and thus, a bottom surface 456 of the flange 450 acts to stabilize the syringe connected thereto in an upright or generally vertical orientation.

Figure 24:
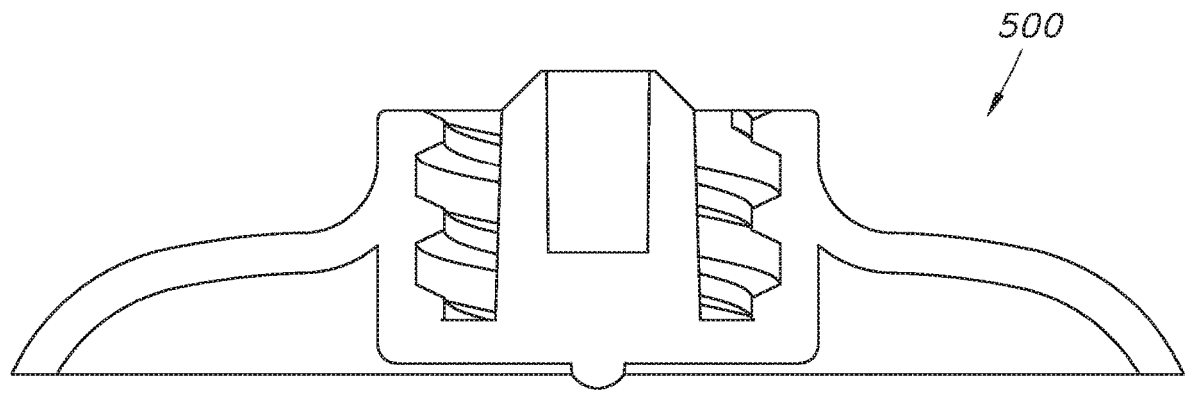
FIG. 24 illustrates a cross-sectional view of a tip cap according to yet another embodiment of the present invention.
Figure 25:
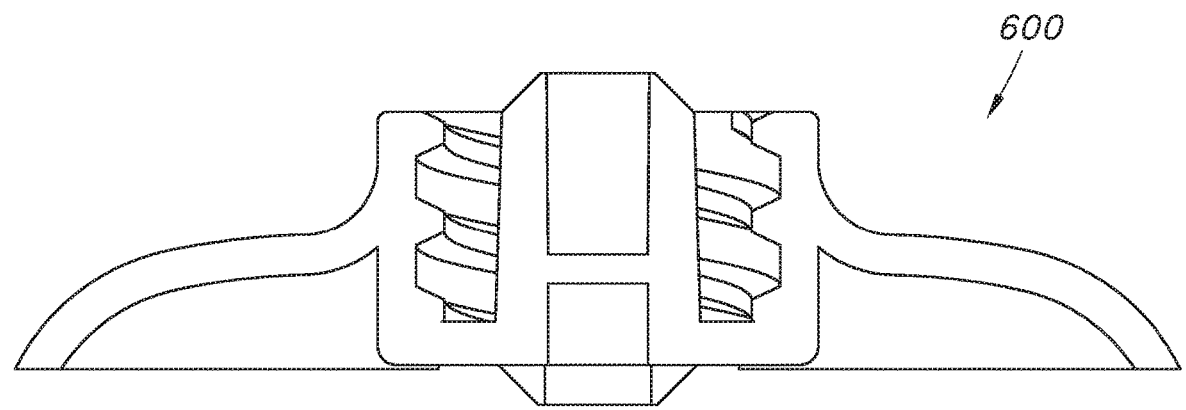
FIG. 25 illustrates a cross-sectional view of a tip cap according to still another embodiment of the present invention.
Figure 26:
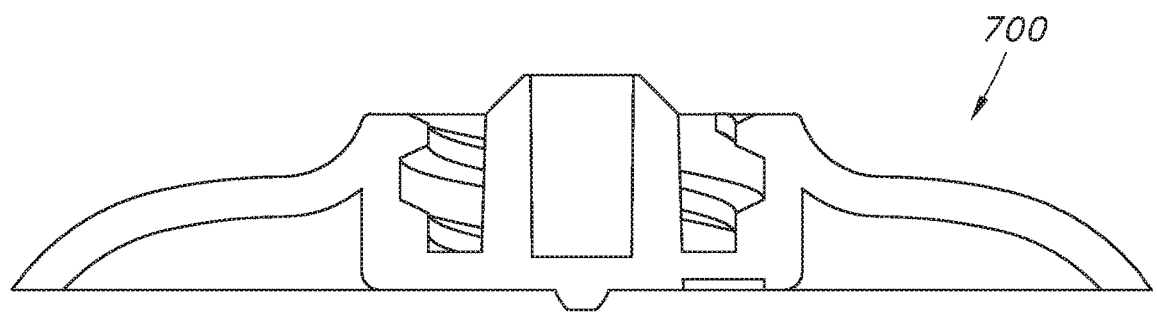
FIG. 26 illustrates a cross-sectional view of a tip cap according to one more embodiment of the present invention.

FIGS. 24-26 show tip caps 500, 600 and 700 according to additional example embodiments of the present invention.

According to another example embodiment, the tip cap can provide a reconfigurable flange, or for example, a flange which can be positioned in either of an assembly configuration and a stand configuration. For example, in the assembly configuration, the flange is positioned so as to maintain its distance from the projection or pivot of the body, and thus, not interfere or cause frictional engagement with the support surface, and thus, allow for an effortless rotational assembly of the tip cap with the syringe (e.g., when the syringe is being pressed against the syringe coupling). And thereafter, the flange can be manipulated such that at least a portion thereof extends beyond an end of the projection, for example, such that the projection does not interfere with the flange so that the flange can engage with the support surface and support the syringe S connected thereto in a substantially upright orientation. According to some example embodiments, the flange can be substantially resilient and/or at least partially flexible so as to permit it to be reconfigurable between the assembly configuration and the stand configuration.

In example embodiments, the tip cap(s) as described herein can preferably be formed from any desirable material including plastics, composites, rubbers, natural materials, synthetic materials, or a combination thereof. According to one example embodiment, the tip cap comprises a high density polyethylene material. According to another example embodiment, the tip cap comprises a polypropylene material. According to another example embodiment, the tip cap comprises two or more materials. Optionally, other materials can be chosen as desired.

According to another example embodiment, the present invention relates to a method of connecting a tip cap with an end connector of a syringe. In example embodiments, the method comprises providing a tip cap, the tip cap comprising a body having a syringe connector at one end and a pivot defining a central point of rotation at the other end, the syringe connector comprising an outer collar surrounding a male hub, the male hub comprising a recess defined therein and having a floor surface, and an inner surface of the outer collar is threaded; providing a syringe comprising a generally elongate barrel having an open end for receiving a plunger and a closed end comprising an end connector, the end connector comprising a projection formed on an outer surface of the end connector; placing the tip cap atop a support surface such that the pivot is generally in contact therewith; grasping the syringe; and engaging the end connector with the syringe connector of the tip cap.

In example embodiments, with the syringe being moved towards the syringe connector, the projection of the end connector rides along the threaded inner surface, thereby causing to tip cap to rotate about the central point of rotation and further entrance of the projection along the threaded inner surface.

In example embodiments, the pivot comprises a post. In alternate example embodiments, the pivot comprises a slightly convex surface. In example embodiments, axial engagement of the end connector with the syringe connector causes the tip cap to self-connect itself to the end connector. In example embodiments, after the pivot of the tip cap is generally facing and engaged with the support surface, the tip cap need not be touched for its attachment to the end connector of the syringe.

In example embodiments, a single one-handed operation of the end connector of the syringe engaging the syringe connector of the tip cap allows for sealingly attaching the tip cap to the end connector.

This written description uses examples to disclose the invention, including the best mode, and also to enable any person skilled in the art to practice the invention, including making and using any devices or systems and performing any incorporated methods. The patentable scope of the invention is defined by the claims and may include other examples that occur to those skilled in the art. Such other examples are intended to be within the scope of the claims if they include structural elements that do not differ from the literal language of the claims or if they include equivalent structural elements with insubstantial differences from the literal language of the claims.

What is claimed is:

1. A tip cap comprising:
   a body extending from a first end to a second end;
   a syringe connector formed at the first end, the syringe connector comprising an outer collar surrounding a male hub, the male hub comprising a recess defined therein and having a floor surface, and an inner surface of the outer collar is threaded; and
   a pivot formed at the second end of the body, the pivot generally being centrally-positioned and axially aligned with the male hub so as to provide a hands-free assembly when an end connector of a syringe is forced against the syringe connector;
   wherein with the pivot resting against a support surface and with the syringe connector generally positioned upright and extending in a direction away from the support surface, the end connector of the syringe is configured to be engaged with the syringe connector, thereby engaging the end connector with the threaded inner surface of the outer collar, and wherein further engagement of the end connector with the syringe connector is configured to cause a portion of the end connector to slide along the threaded inner surface of the syringe connector so as to cause rotation of the body about the pivot, thereby assembling the tip cap with the end connector of the syringe with a single end connector-to-syringe connector operation.

2. The tip cap of claim 1, wherein the end connector of the syringe comprises at least one thread portion for engagement with the threaded inner surface of the outer collar of the syringe connector.

3. The tip cap of claim 1, further comprising a flange extending outwardly from the body, the flange generally positioned between the first and second ends of the body.

4. The tip cap of claim 3, wherein the flange is configured to provide a seal.

5. The tip cap of claim 1, wherein the syringe connector is compatible with the ENFit and ISO 80369-3 design standards.

6. A tip cap comprising:
a central body extending between a first end and a second end;
a syringe coupling provided at the first end of the body, the syringe coupling comprising an outer collar having an inner surface defining a threaded surface and a male projection centrally-positioned within the outer collar;
a central projection provided at the second end of the body, the central projection generally extending in a direction substantially opposite the first end; and
a flange portion generally surrounding at least a portion of the central body and generally being positioned between the first and second ends;
wherein with the second end resting atop a support surface, an end connector of a syringe is engageable with the syringe coupling of the first end such that an outwardly-extending lug of the end connector engages with the threaded surface, such that the body is configured to rotate atop the support surface about the central projection such that the syringe coupling of the first end rotatably connects with the end connector of the syringe.

7. The tip cap of claim 6, wherein the flange portion is substantially cylindrical and outwardly-extends from the central body so as to not pose as a choking hazard.

8. The tip cap of claim 6, wherein the flange comprises a minimum side-to-side dimension of about 1.25 inches.

9. The tip cap of claim 6, wherein the syringe connector is compatible with the ENFit and ISO 80369-3 design standards.

10. The tip cap of claim 6, wherein the flange portion is configured to provide a seal.

* * * * *